United States Patent [19]
De Castro Loureiro Barreto Rosa et al.

[11] Patent Number: 6,103,927
[45] Date of Patent: Aug. 15, 2000

[54] PROCESS FOR THE CARBONYLATION OF ETHYLENICALLY UNSATURATED COMPOUNDS

[75] Inventors: Maria Manuel De Castro Loureiro Barreto Rosa, Amsterdam, Netherlands; Harold Moncrieff Gillespie, Chester, United Kingdom; Arend Kuindert Van Helden, Amsterdam, Netherlands; Paul David Savage, Chester, United Kingdom; Eit Drent, Amsterdam, Netherlands; Eugene Gerard McKenna, Victoria, Australia

[73] Assignee: Shell Oil Company, Houston, Tex.

[21] Appl. No.: 08/835,938

[22] Filed: Apr. 9, 1997

[30] Foreign Application Priority Data

Apr. 16, 1996 [EP] European Pat. Off. .............. 96302633

[51] Int. Cl.$^7$ .................................................. C07C 67/36
[52] U.S. Cl. ........................................... 560/207; 560/104
[58] Field of Search ...................... 560/207, 104

[56] References Cited

U.S. PATENT DOCUMENTS 5,179,225  1/1993  Drent et al. .............................. 560/207

FOREIGN PATENT DOCUMENTS

94/18154  8/1994  WIPO .

*Primary Examiner*—Samuel Barts
*Attorney, Agent, or Firm*—Kim Muller

[57] ABSTRACT

The invention discloses a process for the carbonylation of ethylenically unsaturated compounds by reaction thereof with carbon monoxide and a coreactant in the presence of a catalyst system obtained by combining (a) a source of a Group VIII metal cation (b) a phosphine, arsine or stibine compound acting as a ligand; and (c) a source of anions, other than halide anions, carried out in the presence of substoichiometric amounts of halide anions and/or -in case of a coreactant other than an aromatic alcohol- in the presence of a phenolic promoter. The process provides novel alkylphenol esters that may find use as synthetic lubricant.

22 Claims, No Drawings

PROCESS FOR THE CARBONYLATION OF ETHYLENICALLY UNSATURATED COMPOUNDS

FIELD OF THE INVENTION

The invention relates to a process for the carbonylation of ethylenically unsaturated compounds by reaction with carbon monoxide and a coreactant in the presence of a homogeneous catalyst system comprising a source of Group VIII metal cation and a ligand. It also relates to novel alkylphenol esters so produced and to their use in automotive and industrial applications.

BACKGROUND OF THE INVENTION

Carbonylation reactions are known in the art. For instance, in EP-A-0,495,547 several examples are disclosed wherein olefins are converted into (thio)esters, acids, anhydrides, and amides, etc., depending on the nature of the coreactant. Similarly, in WO 94/18154, a process modification is disclosed, based on the presence of an amine, whereby the rate of the carbonylation reaction as described in EP-A-0,495,547 is increased.

Whilst the process disclosed in WO 94/18154 provides the desired product in better yield and with greater selectivity than in EP-A-0,495,547, further improvement remains desirable. Indeed, there still remain instances where reaction is slow to proceed if at all.

DESCRIPTION OF THE INVENTION

The present invention aims at providing a process with increased reaction rate, without impeding other factors such as selectivity or catalyst stability. Surprisingly, it has now been found that by inclusion into the catalyst system of substoichiometric amounts of halide anions, and/or —in case of a coreactant other than an aromatic alcohol—by the presence of a phenolic compound, the catalyst activity is substantially increased. Accordingly, the invention provides a process for the carbonylation of ethylenically unsaturated compounds by reaction thereof with carbon monoxide and a coreactant in the presence of a catalyst system obtainable by combining (a) a source of a Group VIII metal cation (b) a phosphine, arsine or stibine compound acting as a ligand; and (c) a source of anions, other than halide anions, carried out in the presence of substoichiometric amounts of halide anions and/or —in case of a coreactant other than an aromatic alcohol—in the presence of a phenolic promoter.

It is believed that the carbonylation reactions proceed under the influence of an active catalyst system containing one or more Group VIII metal cations, in complex coordination with the ligand, the ethylenically unsaturated compound and the halide anion and/or the phenolic promoter.

The halide anion can be a chloride, bromide, iodide, or fluoride anion. From a commercial point of view, based on price and availability, the chloride is preferred. From a technical point of view, based on its greater promoting effect and the linearity of the carbonylation products, the iodide anion is preferred.

Substoichiometric in this specification means that less halide anions are present than required to neutralize the Group VIII metal cations. Preferably, the molar ratio of dissociated halide anions versus Group VIII metal cations is less than 2:1, for instance from 0.02:1 to 1:1, per mole of cation. The ideal ratio depends on the liquid medium and may be easily determined by those reasonably skilled in the art. Suitable sources of the halide anion include both hydrogen halides, e.g., HCl, HBr and HI, quaternary ammonium or phosphonium halides, e.g., triphenylmethylphosphonium chloride and metal halides, e.g., NaCl, $MgBr_2$, $ZnCl_2$, $ZnI_2$, LiBr, RbCl, CsCl, CsI, $MgI_2$ and CuCl, in particular alkali or earth alkaline metal halides.

The phenolic promoter is an aromatic compound having one or more hydroxyl groups attached to the aromatic backbone of the compound. Typically, the aromatic backbone is a 6-membered ring, which may be part of a larger fused (aromatic) ring system. Examples of such aromatic compounds include 3-hydroxypyridine, 3- or 6-quinolinol, 1- or 2-hydroxynaphthalene (α- or β-naphthol), o,o'-, m,m'- or p,p'-biphenol, 2,2-di(p-phenylol)propane (DPP), etc. Suitably, it is a 6-membered ring composed of carbon atoms only. More suitably, the aromatic backbone is a benzene ring, optionally having one or more inert groups, such as alkyl groups of up to 20 carbon atoms, thereon attached. For instance, the phenolic promoter may be 3,5-dimethoxyphenol, hydroquinone, or phenol, etc. Preferably, the phenolic promoter is DPP or phenol. The use of the phenolic promoter has been found particularly beneficial in an amount of up to 40% by weight, based on the total weight of reactants, optional solvent and the catalyst system. Preferably, it is used in an amount of 10 to 20% wt.

It will be understood that the phenolic promoter cannot at the same time partake in the carbonylation reaction as coreactant. Therefore, in order for the phenolic promoter to function as promoter, another compound must be present to act as coreactant.

Preferably, the carbonylation process is carried out in the presence both of the phenolic promoter and the halide anion.

The carbonylation reaction is conveniently carried out at moderate temperatures. Accordingly, the process is suitably carried out at a temperature in the range of 30 to 200_C., preferred temperatures being in the range of 50 to 180_C. The reaction pressures may also vary widely. For instance, the reaction can be carried out with pressures in the range of 1 to 200 bar gauge, pressures in the range of 5 to 60 barg being preferred.

Carbon monoxide is preferably supplied in molar excess over the ethylenically unsaturated compound and the coreactant. In addition, the ethylenically unsaturated compound and the coreactant are suitably supplied in a molar ratio within the range of 10:1 to 1:10, preferably within the range of 5:1 to 1:5, more preferably within the range of 2:1 to 1:2.

In the present specification, Group VIII metals (referring to the Periodic Table of the Elements as disclosed in the 61st ed. of the Handbook of Chemistry and Physics) comprise the elements Fe, Co, Ni, Ru, Rh, Pd, Os, Ir and Pt. Preferably the Group VIII metal is a platinum group metal, i.e., Ni, Pd or Pt. Of these, palladium is most preferred.

Examples of suitable sources of the cation are salts, such as salts of the Group VIII metal and nitric acid, sulfuric acid, carboxylic acids having up to 12 carbon atoms in the carboxylate group or sulphonic acid; and metal complexes, e.g., with carbon monoxide or acetylacetonate. Palladium (II) acetate is an example of a suitable source of the preferred cation.

Regarding the phosphine, arsine or stibine compound acting as ligand, monodentate ligands such as triphenylphosphine, etc., may be used. However, preference is given to bidentate ligands containing a second atom that coordinates with the cation, selected from trivalent N, P, As or Sb atoms. Suitably, these bidentate ligands have an organic bridging group that contains 1 to 5 atoms in the bridge between the two coordinating atoms. An example of such a bidentate ligand includes diphenyl(2-pyridyl)arsine.

Preferred bidentate ligands are compounds of the formula $R^1R^2M^1$—R—$M^2R^3R^4$, wherein $M^1$, and $M^2$ independently are P, As or Sb, R represents a bivalent substituted or non-substituted bridging group containing from 1 to 5 atoms in the bridge, $R^1$ and $R^2$ together are a substituted or non-substituted bivalent group whereby the two free valencies are linked to $M^1$, and $R^3$ and $R^4$ together are a substituted or non-substituted bivalent group whereby the two free valencies are linked to $M^2$ or $R^3$ and $R^4$ independently are substituted or non-substituted hydrocarbyl groups.

Regarding the preferred bidentate ligands, $M^1$ and $M^2$ preferably both represent phosphorus atoms. The bivalent bridging group R typically is an organic group, inclusive organometallic groups such as ferrocylene as in WO 95/06027 or ortho-anellated annular systems as in WO 95/30680, connecting the atoms $M^1$ and $M^2$ through carbon atoms. Usually all bridging atoms are carbon atoms, optionally with hetero-atoms (other than H or C) thereto attached. Preferably, R represents an alkylene group containing from 1 to 3 carbon atoms in the bridge, in particular an ethylene group or a propylene group. In the preparation of alkylphenol esters, R ideally represents a propylene group.

The bivalent substituted or non-substituted group, represented by $R^1$ together with $R^2$, preferably contains from 5 to 9 atoms, preferably 8 atoms. Examples of suitable bivalent groups are 1,6-hexylene, 1,6-heptylene, 1,5-octylene, etc. Together with $M^1$, this group forms a phosphacycloalkyl group. Preferably, $R^1$ together with $R^2$ represent a bivalent substituted or non-substituted cyclic group. Together with $M^1$, this preferred group forms a phosphabicycloalkyl group. Examples of suitable bivalent cyclic groups are 1,4-cyclohexylene, 1,4-cycloheptylene, 1,2-cyclooctylene, 1,4-cyclooctylene, 1,5-cyclooctylene and 2-methyl-1,5-cyclooctylene groups.

$R^3$ and $R^4$ may independently represent any substituted or non-substituted hydrocarbyl group, such as alkyl, aryl, alkaryl or aralkyl groups. Preferably, $R^3$ and $R^4$ together have the same meaning as $R^1$ together with $R^2$.

Suitable substituents in case any of R, or $R^1$ to $R^4$ is substituted may be selected from the group consisting of halogen atoms, and cyano, alkoxy, amino and alkylamino groups. The alkyl groups in the alkoxy and alkylamino groups preferably each contain from 1 to 4 carbon atoms.

Particularly preferred bidentate ligands are the [3,3,1] and [4,2,1] isomers of 1,2-P,P'-bis(9-phosphabicyclononyl)ethane, 1,2-P,P'-bis(dimethyl-9-phosphabicyclononyl)ethane, 1,3-P,P'-bis(9-phosphabicyclononyl)propane, 1,3-P,P'-bis(dimethyl-9-phosphabicyclononyl)propane.

For the preparation of the bidentate ligands, reference is made to known techniques, for example the method disclosed in British patent application No. 1,127,965 and Canadian patent application No. 2,086,285.

The catalyst systems used in the process of the invention are further based on a source of anions other than halide anions, i.e., component (c). It is believed that the size of the anion and the distribution of electric charge in the anion significantly contribute to the stability of the catalyst system. Suitably, acids are used as the source of anions, or the salts thereof. Preferably, anions are used that are the conjugated base of acids having a pKa (measured at 18° C. in water) of less than 3, preferably less than 2. The anions derived from these acids are non-coordinating or weakly coordinating with the Group VIII metal cation, by which is meant that little or no covalent interaction occurs between the anion and the cation. Catalysts based on these anions exhibit a substantially improved activity.

Suitable anions include anions derived from Bronsted acids, such as from phosphoric acid and sulfuric acid, and in particular from sulphonic acids and (halogenated) carboxylic acids, such as trifluoroacetic acid, 2,6-dichlorobenzoic acid, and 2,6-bis(trifluoromethyl)benzoic acid or trifluoroacetic acid, etc. Anions derived from sulphonic acids are particularly preferred, for example methanesulphonic acid, trifluoromethanesulphonic acid, tert-butanesulphonic acid, p-toluenesulphonic acid and 2,4,6-trimethylbenzenesulphonic acid.

Also, complex anions are suitable, such as the anions generated by a combination of a Lewis acid such as BF3, B(C6F5)3, AlCl3, SnF2, Sn(CF3SO3)2, SnCl2 or GeCl2, with a protic acid, preferably having a pKa of less than 5, such as a sulphonic acid, e.g. CF3SO3H or CH3SO3H or a hydrohalogenic acid such as HF or HCl, or a combination of a Lewis acid with an alcohol. Examples of such complex anions are BF4-, SnCl3-, [SnCl2.CF3SO3]- and PF6-.

When an organic or inorganic base is present, e.g., as further catalyst promoter, anions derived from acids having a pKa in the range of 6 to 3 may also be used. Examples thereof include carboxylic acids.

The quantity in which the catalyst system is used, is not critical and may vary within wide limits. Usually amounts in the range of $10^{-8}$ to $10^{-1}$, preferably in the range of $10^{-7}$ to $10^{-2}$ mole atom of component (a) per mole of ethylenically unsaturated compound are used.

For the preparation of the catalyst systems of the invention, the amount of ligand is generally applied in some excess of the amount of the Group VIII metal cation, expressed as moles of ligand per mole atom of the cation. Typically the amount of ligand is selected such that per mole atom of the cation 0.5 to 10 moles of ligand are present. However, for the preferred catalyst system the active species is believed to be based on an equimolar amount of bidentate ligand per mole cation. Thus, the molar amount of bidentate ligand per mole of cation is preferably in the range of 1 to 3, more preferably in the range of 1 to 2. In the presence of oxygen, slightly higher amounts may be beneficial. The amount of the anion source may range from 0.5 to 15, preferably from 1 to 8 moles per mole of cation.

If desired, the reaction may be performed in the presence of a further catalyst promoter, such as an organic or inorganic base. Suitably, an amine is used. The amine is typically a cyclic amine or a tertiary amine. A preferred further catalyst promoter is triethylamine. The amine may be used in large amounts. Suitable amounts include up to 1000, e.g., from 1 to 20 moles per mole of cation. In particular in the carbonylation of (cyclo)alkadienes, and or the carbonylation with (substituted) phenols as coreactant, the presence of the further catalyst promoter has been found very beneficial.

In the process of the invention, the starting materials and the formed carbonylation products may act as reaction diluent. Hence, the use of a separate solvent is not necessary. Conveniently, however, the carbonylation reaction may be carried out in the additional presence of a solvent. As such, saturated hydrocarbons, e.g. paraffins and isoalkanes are recommended and furthermore ethers such as 2,5,8-trioxanonane (diglyme), diethylether and anisole; sulphones such as sulpholane, and aromatic hydrocarbons such as toluene.

The ethylenically unsaturated compound may have one or more double bonds and is preferably an olefin having from 2 to 30 carbon atoms per molecule. The unsaturated bond(s) may be internal or, preferably, terminal. In particular preferred are olefins having from 2 to 22 carbon atoms per molecule, such as ethene, propene, 1-butene, 1-hexene, 1-octene, 1-dodecene and 1-octadecene.

In the ethylenically unsaturated compound one or more hydrogen atoms may have been substituted by other atoms, such as halogen atoms or by groups of atoms, such as hydroxyl groups, cyano groups, such as methoxy or ethoxy groups, or amino groups such as dimethyl- and diethylamino groups.

Another preferred category of ethylenically unsaturated compounds, consists of unsaturated esters of carboxylic acids and esters of unsaturated carboxylic acids. For example, the starting material may be a vinyl ester of a carboxylic acid such as acetic acid or propanoic acid, or it may be an alkyl ester of an unsaturated acid, such as the methyl or ethyl ester of acrylic acid or methacrylic acid.

A further preferred category of ethylenically unsaturated compounds, consists of cycloalkadienes, which will ordinarily refuse carbonylation. For example, the starting material may be dicyclopentadiene or norbornadiene, to give diesters, diamides or diacids, etc., which may find use as monomer in polymerization reactions.

Suitable coreactants in the process of the invention include compounds comprising a nucleophilic moiety and a mobile hydrogen atom.

Preferred nucleophilic compounds include: water and alcohols, e.g., monohydric alcohols, such as methanol, ethanol, isopropanol and 1-butanol, and polyhydric alcohols, such as ethyleneglycol, 1,4-butanediol and glycerol; thiols; primary or secondary (poly)amines or amides, such as diethylamine, N,N-dimethyl ethylenediamine; aromatic alcohols and carboxylic acids, for example acetic acid, pivalic acid and propanoic acid. Monohydric alcohols having from 1 to 6 carbon atoms per molecule and dihydric alcohols having from 2 to 6 carbon atoms per molecule are preferred.

1-Butanol, methanol and 1,4-butanediol are especially preferred. The use of these compounds as coreactants enables the production of valuable carbonylation products, such as methyl propanoate, butyl propanoate and 1,4-diacyloxy butanes. These compounds are of commercial interest and may be used as solvents and in flavoring compositions and perfumes.

Another preferred class of coreactants is composed of alkyl-phenols, wherein one or more alkyl groups of up to 30, typically 6 to 22 carbon atoms are attached to the phenol molecule.

Carbonylation of these coreactants produces novel alkylphenyl esters. These alkylphenyl esters may find use as synthetic lubricants in industrial application, but in particular in automotive engines, since exhibiting a very low volatility combined with a low viscosity and a high oxidation stability. These characteristics give the alkylphenyl esters a significant advantage over existing lubricants when considering two important requirements for future lubricants: increasing fuel economy and lowering emissions. Besides, they exhibit excellent hydrolytic stability, good cleanliness performance and good elastomer compatibility.

Thus, the invention also provides novel alkylphenyl esters of the general formula

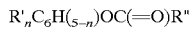

$R'_n C_6 H_{(5-n)} OC(=O)R''$ wherein R' is an alkyl group of 1 to 30 carbon atoms, suitably of 4 to 22 carbon atoms, n is an integer of 1 to 5, typically 1 or 2, and R" is an alkyl group of 2 to 30 carbon atoms, suitably of 4 to 22 carbon atoms. Preferably, n is 1, and R' together with R" have from 20 to 40 carbon atoms. More preferably, the number of carbon atoms in R' is larger than the number of carbon atoms in R". The starting alkylphenol is suitably prepared by alkylation of the phenol. For instance, they may be prepared by alkylation of a phenol with an alpha or internal olefin, e.g., such as an alpha olefin with 14 to 18 carbon atoms. These novel alkylphenol esters may also be prepared through esterification, e.g., by reaction of the alkyl-phenol with the carboxylic acid or corresponding acid chloride.

The invention further provides the use of the novel class of alkylphenyl esters as synthetic lubricant, for instance in automotive applications. In particular the alkylphenyl esters wherein R' together with R" have from 20 to 40 carbon atoms exhibit attractive properties regarding viscosity, oxidative stability and volatility. Those wherein the number of carbon atoms in R' is larger than the number of carbon atoms in R" exhibit an attractive pour point (low). Oxidative stability and pour point may be further improved by incorporation of branched alkyl groups, either R' (alkylation with an internal or branched olefin) or R" (carbonylation of an internal or branched olefin).

Finally, in accordance with the present invention there is also provided a lubricating oil composition comprising as a base fluid an alkylphenol ester as mentioned above. In the lubricating oil composition, the alkylphenol ester may be present in an amount of at least 2% by weight, preferably at least 10% w/w, more preferably at least 40% w/w of the total base fluid. It may be present in an amount up to 100% w/w, preferably up to 90% w/w, more preferably up to 75% w/w on the same basis. It should be understood, however, that the amount of alkylphenol ester may vary with the price-performance aimed at. Furthermore, in the lubricating oil composition according to the present invention, the balance of the total base fluid is preferably a base oil of mineral or synthetic origin.

Suitable additives with which the compounds of the present invention may be used for engine oil application may include one or more extreme pressure/anti-wear agents, for example zinc salts such as zinc dialkyl or diaryl phosphorodithioates (at a concentration giving from 0 to 0.15% w/w phosphorus in the lubricating oil composition); one or more overbased metal-containing detergents such as calcium or magnesium alkyl salicylates or alkylarylsulphonates (present at total detergent concentration in the lubricating oil composition from 0 to 20% w/w); one or more detergents such as phenates and phenate/sulphonate mixtures (present at total detergent concentration in the lubricating oil composition from 0 to 20% w/w); one or more ashless dispersant additives such as reaction products of polyisobutenyl succinic anhydride and an amine or ester (present at total dispersant active matter concentration in the lubricating oil composition from 0 to 20% w/w); optionally one or more primary antioxidants, for example hindered phenols or amines (present at concentrations in the lubricating oil composition from 0 to 5% w/w). Other supplementary additives, for example anti-rust or friction-modifying additives may optionally be present. Viscosity Index improving polymers may optionally be present at polymer concentrations from 0 to 20% w/w. Pour point depressing additives may optionally be present at concentrations from 0 to 5% w/w.

The balance of base oil in the lubricating oil composition may be a base oil of mineral or synthetic origin. Base oils of mineral origin may be mineral oils, for example produced by solvent refining or hydroprocessing. Base oils of synthetic origin may typically be mixtures of $C_{10-50}$ hydrocarbon polymers, for example liquid polymers of alpha-olefins. They may also be conventional esters, for example polyol esters. The base oil may also be a mixture of these oils. Preferably the base oil is that of mineral origin sold by the Royal Dutch/Shell Group of Companies under the designations "HVI" or, most preferably, the synthetic hydrocarbon base oils sold by the Royal Dutch/Shell Group of Companies under the designation "XHVI".

EXAMPLE

The invention will now be further described in the following examples, however, without restricting its scope. All experiments were carried out in a magnetically stirred 250 ml autoclave unless otherwise indicated. The abbreviations used in the Tables have the following meanings:

BCPE=1,2-P,P'-bis(9-phosphabicyclo[3,3,1 or 4,2,1] nonyl)ethane;

BCPP=1,3-P,P'-bis(9-phosphabicyclo[3,3,1 or 4,2,1] nonyl)propane;

MSA=methanesulphonic acid;

DPP=2,2-di(p-phenylol)propane.

Example 1

(Comparative)

The autoclave was charged with 20 ml of butanol, 40 ml of butyl propanoate (solvent), 0.25 mmol of palladium(II) acetate, 0.6 mmol of BCPE, 0.5 mmol of MSA and 5 ml of triethylamine. After being flushed, the autoclave was pressurized with carbon monoxide and ethene to a partial pressure of 15 bar and 10 bar respectively. Next, the reactor was sealed. The contents of the autoclave were heated to a temperature of 125° C. and maintained at that temperature for 2 hours. After cooling, a sample was taken from the contents of the autoclave and analyzed by Gas Liquid Chromatography.

Ethene was fully converted with 100% selectivity into butyl propanoate at an average rate of 300 mol per mole Pd per hour (mol/mol.hr). Similar results were found in the presence of 1 ml triethylamine.

Example 2

The experiment of Example 1 was repeated, however, in the presence of 0.25 mmol HCl.

Ethene was now fully converted with 100% selectivity into butyl propanoate at an average rate of 1200 mol/mol.hr.

Example 3

The experiment of Example 1 was repeated, however, in the presence of 2 mmol propanoic acid instead of MSA and in the presence of 10 g DPP.

Ethene was now fully converted with 100% selectivity into butyl propanoate at an average rate of 1200 mol/mol.hr. When phenol is used instead of DPP, an average rate was found of 1200 mol/mol.hr.

Example 4

The experiment of Example 1 was repeated, however, in the presence of 0.25 mmol HCl and 5 g phenol.

Ethene was now fully converted with 100% selectivity into butyl propanoate at an average rate of 4000 mol/mol.hr. When 10 g of phenol were used, the average rate increased to 8000 mol/mol.hr. An average rate of 8000 mol/mol.hr was also found when 10 g of DPP instead of phenol, and triphenylmethylphosphonium chloride instead of HCl were used.

Example 5

The experiment of Example 1 was repeated, however, without triethylamine and 1 mmol of propanoic acid instead of MSA, and in the presence of 0.25 mmol HCl and 10 g phenol.

Ethene was now fully converted with 100% selectivity into butyl propanoate at an average rate of 7000 mol/mol.hr. When 2 ml of triethylamine were added, the average rate increased to 8000 mol/mol.hr.

Example 6

The autoclave was charged with 20 ml 1-octene, 15 ml N,N-dimethyl-1,3-propanediamine, 40 ml toluene, 0.25 mmol of palladium(II) acetate, 0.6 mmol BCPE, 0.5 mmol MSA, 0.25 mmol NaCl and 10 g of -naphthol. After being flushed, the autoclave was pressurized with 20 bar carbon monoxide. Next, the reactor was sealed. The contents of the autoclave were heated to 145° C. and maintained at that temperature for 5 hours. After cooling, a sample was taken from the contents of the autoclave and analyzed by GLC.

The product, (N,N-dimethyl-3-aminopropyl)nonanamide, was formed with a linearity of 92%. An olefin conversion of 50% was reached, corresponding to an average rate of 300 mol/mol.hr.

Example 7

Example 6 was repeated, however, with NaI instead of NaCl. Besides, the contents of the autoclave were now heated for 1 hour.

The product was formed with a linearity of 97%, whereas an olefin conversion of 60% was reached. This corresponds to an average rate of 1500 mol/mol.hr.

Example 8

Example 7 was repeated, however, at 125 C. instead of 145 C. The contents of the autoclave were now heated for 1.5 hours.

The product was now formed with a linearity of 98.5%, whereas an olefin conversion of 80% was reached. This corresponds to an average rate of 1000 mol/mol.hr.

Example 9

The autoclave was charged with 20 ml 1-octene, 15 ml 2-aminoethanol, 40 ml diglyme, 0.25 mmol of palladium(II) acetate, 0.6 mmol BCPE, 0.5 mmol MSA, 0.25 mmol NaI and 5 g of phenol. After being flushed, the autoclave was pressurized with 20 bar carbon monoxide. Next, the reactor was sealed. The contents of the autoclave were heated to 175 C. and maintained at that temperature for 1 hour. After cooling, a sample was taken from the contents of the autoclave and analyzed by GLC.

The product, (2-ethylol)nonanamide, was formed with a linearity of 97%. An olefin conversion of 60% was reached, corresponding to an average rate of 1500 mol/mol.hr.

Example 10

Using the same catalyst as in Example 9, 10 ml 1,7-octadiene was carbonylated at 150 C. and 15 bar CO with 40 ml methanol. The contents of the autoclave were heated for 10 hours. The product was analyzed to find it composed for 90% of diesters (48% linear), produced at an average rate of 40 mol/mol.hr and an octadiene conversion of 95%.

Example 11

The autoclave was charged with 20 ml 1-octene, 20 g phenol, 40 ml toluene, 0.25 mmol of palladium(II) acetate, 0.6 mmol BCPP, 0.5 mmol MSA, 0.25 mmol NaCl and 0.2 ml triethylamine. After being flushed, the autoclave was pressurized with 20 bar carbon monoxide. Next, the reactor was sealed. The contents of the autoclave were heated to 150 C. and maintained at that temperature for 1.5 hours. After cooling, a sample was taken from the contents of the autoclave and analyzed by GLC.

The product, phenyl nonanoate, was formed with a linearity of 70%. An olefin conversion of 80% was reached, corresponding to an average rate of 1200 mol/mol.hr.

Example 12

Example 11 was repeated, however, using LiBr instead of NaCl, at a temperature of 125 C. Besides, the contents of the autoclave were heated for 1 hour.

Phenyl nonanoate was now formed with a linearity of 83%. An olefin conversion of 50% was reached, corresponding to an average rate of 1500 mol/mol.hr.

Example 13

Example 11 was repeated, however, using NaI instead of NaCl, at a temperature of 125 C.

Phenyl nonanoate was now formed with a linearity of 86%. An olefin conversion of 90% was reached, corresponding to an average rate of 1200 mol/mol.hr.

Example 14

The autoclave was charged with 5 ml dicyclopentadiene, 40 ml methanol, 0.25 mmol of palladium(II) acetate, 0.6 mmol BCPE, 0.5 mmol MSA, 0.25 mmol NaI, 2 ml triethylamine and 5 g of phenol. After being flushed, the autoclave was pressurized with 20 bar carbon monoxide. Next, the reactor was sealed. The contents of the autoclave were heated to 155° C. and maintained at that temperature for 10 hours. After cooling, a sample was taken from the contents of the autoclave and analyzed by GLC.

The product was analyzed and found to be composed for 64% of diesters and 36% of monoesters (by mole). The product was formed at 100% DCPD conversion and an average rate of 30 mol/mol.hr.

At a temperature of 165 C., the diester content increased to 70%, and the average rate to 100 mol/mol.hr.

Example 15

Example 14 was repeated, however, using 10 g phenol (155 C.). The diester content increased to 80%, and the average rate to 150 mol/mol.hr.

Example 16

Example 14 was repeated, however, using 10 g -naphthol or 3,5-dimethoxyphenol (155 C.). The diester content in each experiment increased to 84%, and the average rate to 200 mol/mol.hr.

Example 17

A hexadecylphenol was prepared by alkylating phenol with 1-hexadecene in the presence of 2% by weight of an acidic zeolite as catalyst.

The autoclave was charged with 11 ml 1-octene, 41.75 g of the hexadecylphenol, 26 g sulpholane, 0.25 mmol of palladium(II) acetate, 0.6 mmol BCPP, 0.5 mmol MSA, 0.10 mmol HCl and 1.65 ml triethylamine. After being flushed, the autoclave was pressurized with 17.7 bar carbon monoxide. Next, the reactor was sealed. The contents of the autoclave were heated to 140 C. and maintained at that temperature for 6 hours. After cooling, a sample was taken from the contents of the autoclave and analyzed by GLC.

Hexadecylphenyl nonanoate was formed at 61.5% hexadecylphenol conversion with 100% selectivity at an average rate of 187 mol/mol.hr.

Example 18

A $C_{4-18}$-alkylphenol was prepared by alkylating phenol with a mixture of $C_{14-18}$-1-alkenes in the presence of 2% by weight of an acidic zeolite as catalyst.

The autoclave was charged with 18.3 ml 1-dodecene, 39.7 g (122 mmol) of the $C_{14-18}$-alkylphenol, 25 g sulpholane, 0.26 mmol of palladium(II) acetate, 0.66 mmol BCPP, 0.10 mmol HCl and 1 ml triethylamine. After being flushed, the autoclave was pressurized with 16.4 bar carbon monoxide. Next, the reactor was sealed. The contents of the autoclave were heated to 125° C. and maintained at that temperature for 6 hours. After cooling, a sample was taken from the contents of the autoclave and analyzed by GLC.

The $C_{14-18}$-alkylphenyl tridecanoate was formed at 76.2% alkylphenol conversion with 100% selectivity at an average rate of 188 mol/mol.hr.

Example 19

The properties of the products of examples 17 and 18 were analyzed in respect of i) the kinematic viscosity at 100° C. (Vk100); ii) viscosity index (VI); iii) pour point (PP); iv) volatility (as measured by ThermoGravimetric Analysis); v) oxidation stability (as measured by Differential Scanning Calorimetry); seal swell; and deposit formation (as measured by the Wolf Strip Test method). Besides, the products have been compared with two commercial esters: BISOFLEX TOT, trademark for a 2-ethylhexyl trimellitate; and PRIOLUBE 3939, a trademark for an ester of pentaerythritol and $C_{5-9}$ linear acid.

Table 1 shows the physical properties of the alkylphenol esters of the present invention as compared to the commercially available products.

The Vk100 of an oil is measured under low shear conditions (gravity). The viscosity index (VI) is a number indicating the effect of change of temperature on the Vk of an oil. A high VI signifies relatively small change of Vk with temperature, which is desirable. The Vk100 was determined according to ASTM D 445-94; the VI was calculated according to ASTM D 2270-86.

The pour point is defined at the lowest temperature at which an oil will flow when cooled at a specific rate. In crankcase use, a low pour point is desirable. Pour point has been determined according to ASTM D 97-87.

The oxidation stability of the alkylphenol esters was evaluated by DSC. DSC measures the differential heat flow when a sample of oil in a small pan and an empty pan (reference) are heated under an oxygen or air atmosphere in a closed cell. Typically, a 2 mg sample of oil is used in an open aluminum pan. The measurements were designed to mimic oil conditions encountered in automotive engine lubrication. In temperature programmed (dynamic) experiments, the test temperature was increased linearly from 40 to 350° C. at 20 C/min. The cell atmosphere was 205 kPa $O_2$, and the gas flow rate 60 10 ml/min. The onset of rapid oxidation is marked by a rapidly increasing exotherm. The extrapolated onset temperature is defined by the intersection of the tangent at the steepest part of the increasing exotherm and the baseline extrapolated from lower temperatures, on a plot of power versus temperature. For neat fluids, a DSC onset temperature value above about 220° C. is considered good.

Weight loss up to 262° C. was determined according to method IP 393/91 from the record of mass loss as a function of temperature in a suitable ThermoGravimetric instrument, run at a constant heating rate of 10° C./min from 40 to 550° C. under flowing nitrogen. This measurement has been shown (based on a limited correlation exercise) to provide an indication of the evaporative loss (=volatility) from an oil held at 250_C. (the "Noack method"). A low volatility (low volatile loss at high temperature) is desirable.

Seal swell was evaluated according to test method IP 278/72. A value of 9, as found for a 80:20 w/w blend of a commercially available synthetic base oil (referred to hereinafter as the reference oil) and PRIOLUBE 3939, is still acceptable, although a lower seal swell is desirable to reduce wear.

The Wolf Strip test (based on method DIN 51392) is an inclined hot plate test, where the lubricant under test is circulated at 50 ml/min. for a number of hours over a hot metal test strip, that is 8_declined against the horizontal. The weight of deposit remaining on the test strip is recorded at the end of the test. A low deposit is desirable.

TABLE 1

| Properties | Exp. 17 | Exp. 18 | PRIOLUBE 3939 | BISOFLEX TOT |
|---|---|---|---|---|
| Vk100 (cSt) | 5.5 | 6.3 | 4.9 | 8.4 |
| VI | 131 | 140 | 143 | 50 |
| Pour Point (° C.) | −30 | −15 | −57 | −30 |
| TGA (%) | 2.8 | 1.5 | 4.0 | 4.2 |
| DSC (° C.) | 225 | 217 | 210 | 218 |
| Seal swell | 7.3 | 2.6 | 27 | 31 |
| Wolf strip (mg) (base oil:ester) | 313 | 594 | 777 | 160 |
| neat | 16–40 | n.d. | 115 | 10–32 | n.d. not determined

It will be apparent to the skilled reader that the alkylphenol esters not only exhibit the desirable combination of low viscosity with low volatility, but also exhibit a low seal swell and perform well in the wolf strip test.

Example 20

A $C_{14-18}$-alkylphenyl dodecanoate was tested in a fully formulated oil for diesel applications. The alkylphenol ester, at either 30 or 60% w/w concentration, was blended with the reference oil used previously and detergent and ash levels in the mid range of current commercially available diesel engine oils.

Oxidation stability of the blend containing the alkylphenol ester was tested by comparing the induction periods during isothermal Differential Scanning Calorimetry with blends containing a commercial polyol ester. The IP was measured at 200 and 210_C. Long IP's are preferable. The test results are set out in Table 2. These test results show that the alkylphenol ester at 30% concentration shows an oxidation stability benefit over similarly formulated synthetic base fluids, containing either polyol esters (PRIOLUBE 3939 and 3970, ex UNICHEMA), a trimellitate ester (REOLUBE OTM, ex FMC) or a carbonate ester (AGIP MX2201, ex AGIP Petroli/ENICHEM AUGUSTA JV) at equivalent concentrations at both 200 and 210° C. The alkylphenol ester at 60% concentration shows a twofold increase in induction period compared with the blend of reference oil containing the same detergent and ash levels and an appreciable benefit compared with the commercial carbonate ester.

TABLE 2

INDUCTION PERIODS BY ISOTHERMAL DSC

| Composition | at 200° C./min | at 210°/min |
|---|---|---|
| reference oil | 14 | 8 |
| 30% alkylphenol ester | 22 | 12 |
| 30% PRIOLUBB 3939 | 19 | 8 |
| 30% PRIOLUBE 3970 | 17 | 9 |
| 30% REOLUBE OTM | 18 | 9 |
| 30% AGIP MX2201 | 20 | 10 |
| 60% alkylphenol ester | 28 | 14 |
| 60% AGIP MX2201 | 23 | 9 |

Example 21

The 60% w/w lubricating oil composition of Example 20 was subjected to a caterpillar micro oxidation test, which is a laboratory bench text used to predict the lubricant deposit-forming tendencies under thin film conditions. Accordingly, samples are subjected to 230° C. under air with a set flow rate to oxidize oil and cause deposit-formation on a pre-weighed metal coupon. Deposits are then weighed and the accumulation of deposits determines the induction time. An induction period of 275 minutes was found, as compared to 115 minutes for the reference oil.

Example 22

An MWM-B Diesel Engine test (pursuant test method CEC L-12-A-76) was conducted to evaluate the 60% w/w lubricating oil composition of Example 20 as crankcase oil in respect of piston deposits and ring sticking. The higher the piston rating, the better the composition's performance. As may be learned from Table 3, the alkylphenol ester at this concentration dramatically improves the cleanliness ratings in many piston regions and in particular the top groove (i.e., groove 1), land 1 and undercrown as compared with the reference oil.

TABLE 3

| Lubricating oil composition | reference oil | 60% alkylphenol ester |
|---|---|---|
| Groove 1 | 0.7 | 16 |
| Land 1 | 64.3 | 81.5 |
| Groove 2 | 94.9 | 95.1 |
| Land 2 | 93.0 | 89.5 |
| Groove 3 | 100 | 98.3 |
| Mean | 70.6 | 76.9 |
| undercrown | 65 | 79 |

What is claimed is:

1. A process for carbonylation of ethylenically unsaturated compounds comprising reaction thereof with carbon monoxide and a coreactant, said reaction being performed in the presence of substoichiometric amounts of halide anions and a catalyst system comprising (a) a source of a Group VII metal cation (b) a ligand comprising a compound selected from the group consisting of phosphine, arsine or stibine compound; and (c) a source of anions, other than halide anions.

2. The process of claim 1 further including performing said reaction in the presence of a phenolic promoter when said coreactant is other than an aromatic compound.

3. The process of claim 1 wherein said substoichiometric amounts of halide anions include substoichiometric amounts of chloride and iodide anions.

4. The process of claim 1 wherein said halide anions and said Group VIII cations have a molar ratio of between about 0.02:1 to about 2:1.

5. The process of claim 2, wherein said phenolic promoter is an aromatic compound having at least one hydroxyl groups attached to aromatic backbone of the compound.

6. The process of claim 2, wherein said phenolic promoter is in amounts of between about 10% to about 40% by weight of all reactants.

7. The process of claim 1 performed at a temperature range of about 100° C. to about 200° C.

8. The process of claim 1 performed at a pressure range of about 1 to about 200 bar gauge.

9. The process of claim 1, wherein carbon monoxide is supplied in molar excess over said ethylenically unsaturated compound and said coreactant.

10. The process of claim 1, wherein said ethylenically unsaturated compound and said coreactant are supplied in a molar ratio of between about 10:1 to about 1:10.

11. The process of claim 1, wherein said source of Group VIII metal cation is a platinum group metal compound.

12. The process of claim 11 wherein said platinum group metal compound includes a palladium metal compound.

13. The process of claim 1, wherein said ligand includes a bidentate ligand having an atom coordinating with a cation selected from trivalent nitrogen, phosphine, arsine, and stibine atoms.

14. The process of claim 13, wherein said bidentate ligand is a compound represented by the formula $R^1R^2M^1$—R—$M^2R^3R^4$, wherein $M^1$ and $M^2$ are independently selected from the group consisting of phosphine, arsine and stibine, R represents a bivalent substituted or non-substituted bridging group having at least one carbon atom, $R^1$ and $R^2$ together are a substituted or non-substituted bivalent group having two free valencies linked to $M^1$, and $R^3$ and $R^4$ together are a substituted or non-substituted bivalent group having two free valencies linked to $M^2$, or $R^3$ and $R^4$, independently, are a substituted or non-substituted hydrocarbyl group.

15. The process of claim 14, wherein $M^1$ and $M^2$ represent phosphorus atoms.

16. The process of claim 14, wherein said bivalent bridging group, represented by R contains about 1 to about 5 carbon atoms.

17. The process of claim 14, wherein said substituted or non-substituted bivalent group represented by $R^1$ together with $R^2$ contains about 5 to about 9 atoms.

18. The process of claim 14, wherein said substituted or non-substituted bivalent group represented by $R^1$ and $R^2$ further includes a cyclic group.

19. The process of claim 18, wherein said cyclic group includes a group selected from 1,4-cyclohexylene, 1,4-cycloheptylene, 1,3-cycloheptylene, 1,2-cyclooctylene, 1,3-cyclooctylene, 1,4-cyclooctylene, 1,5-cyclooctylene, 2-methyl-1,5-cyclooctylene, 2,6-dimethyl-1,4-cyclooctylene and 2,6-dimethyl-1,5-cyclooctylene groups.

20. The process of claim 13, wherein said bidentate ligand includes ligands selected from a group consisting of [3,3,1] and [4,2,1] isomers of 1,2-P,P'-bis(9-phosphabicyclononyl)ethane, 1,2-P,P'-bis(dimethyl-9-phosphabicyclononyl)ethane 1,3-P,P'-bis (9-phosphabicyclononyl)propane, and 1,3-P,P'-bis(dimethyl-9-phosphabicyclononyl)propane.

21. The process of claim 1, wherein said anion source is derived from acids having a pKa of less than 3, measured in aqueous solution at 18° C.

22. The process of claim 2, wherein said phenolic promoter is an alkylphenol having at least one alkyl groups of up to 30 carbon atoms attached to the phenol molecule.

* * * * *